(12) United States Patent
Iwaki et al.

(10) Patent No.: US 7,235,357 B2
(45) Date of Patent: Jun. 26, 2007

(54) METHOD OF REDUCING BACKGROUND IN FLUORESENCE DETECTION

(75) Inventors: Yoshihide Iwaki, Asaka (JP); Hiroshi Shinoki, Asaka (JP); Osamu Seshimoto, Asaka (JP); Kouki Nakamura, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 415 days.

(21) Appl. No.: 10/179,395

(22) Filed: Jun. 26, 2002

(65) Prior Publication Data
US 2003/0044830 A1    Mar. 6, 2003

(30) Foreign Application Priority Data

Jun. 27, 2001  (JP) .............................. 2001-194787
Feb. 28, 2002  (JP) .............................. 2002-052740

(51) Int. Cl.
*C12Q 1/68* (2006.01)
*C12P 13/16* (2006.01)
*C07C 61/00* (2006.01)
*C07C 229/00* (2006.01)

(52) U.S. Cl. .......................... 435/6; 435/112; 562/400; 562/575

(58) Field of Classification Search .................... 435/6, 435/112; 562/400, 575
See application file for complete search history.

(56) References Cited

U.S. PATENT DOCUMENTS 6,312,906 B1 * 11/2001 Cass et al. ..................... 435/6
6,642,001 B1 * 11/2003 Bolk et al. ..................... 435/6

FOREIGN PATENT DOCUMENTS

| JP | 2001-228152 A | 8/2001 |
| JP | 2002-176977 A | 6/2002 |
| WO | WO 97/14815 | 4/1997 |

OTHER PUBLICATIONS

Patrick O. Brown et al.; Genome Research; vol. 6, pp. 639-645, 1996.
Richard A. Cardullo et al.; Proc. Natl. Acad. Sci., vol. 85, pp. 8790-8794, 1988.
Molecular Cloning: Appendix A1.14-A1.16, Jan. 15, 2001.

* cited by examiner

*Primary Examiner*—Jezia Riley
(74) *Attorney, Agent, or Firm*—Birch, Stewart, Kolasch, Birch, LLP

(57) ABSTRACT

The present invention provides a method for detecting fluorescence by using a solid support to which a probe molecule to be detected is fixed, wherein background is reduced by using a quenching agent. By using present invention, detection sensitivity of a DNA chip can be increased and stable data can be obtained.

16 Claims, No Drawings

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: U primer directed to Homo sapiens liver

<400> SEQUENCE: 1
acccccggaa aacacgcaca gt                    22

<210> SEQ ID NO 2
<211> LENGTH: 25
<212> TYPE: DNA
<213> ORGANISM: Artificial Sequence
<220> FEATURE:
<223> OTHER INFORMATION: L primer directed to Homo sapiens liver

<400> SEQUENCE: 2
tcaggcactt tcattaacag gcaca                 25

METHOD OF REDUCING BACKGROUND IN FLUORESENCE DETECTION

TECHNICAL FIELD

The present invention relates to a method of reducing background in fluorescence detection. More particularly, the present invention relates to a method of reducing background in fluorescence detection which is performed on a simultaneous analysis of expression, mutation, polymorphism or the like of gene with a DNA chip. Further, the present invention particularly relates to a blocking solution for the purpose of enhancement of detection sensitivity and acquirement of stable data using the DNA chip.

BACKGROUND ART

The blocking reagents which is used when a gene is detected by using a nylon membrane or a nitrocellulose membrane, include Denhalt reagent (50× Denhalt solution: 1% (w/v) Ficoll, 1% (w/v) polyvinyl pyrrolidone, 1% (w/v) bovine serum albumin), heparin, and skim milk. However, even by use of these blocking reagents, a blocking effect is not satisfactory, and sometimes a reproducible result cannot be obtained.

In the case where a slide glass is used as a substrate, a method is reported in which the slide glass coated with poly-L-lysine is blocked with succinic anhydride (P. O. Brown et al., Genome Res, 1996; 6: 639–645; Japanese Patent Laid-open Publication No. H11-514872). This method tries to delete a charge of an amino group by coupling the amino group on the slide glass with succinic anhydride. However, this method has various problems other than the blocking of the amino group.

For example, since the slide glass is immersed in a solution during blocking, DNA which was spotted to the slide glass was washed off during blocking, resulting in nonspecific adsorption, not good appearance, and no reproducibility, or the like. Thus, reliability of obtained data was insufficient.

In the case where a DNA chip is utilized, a fluorescence labeled-compound is often used for detection. Since such labeled compounds usually have a charge (since fluorescent dyes contain a sulfone group ($-SO_3H$) in many cases), DNA labeled with these compounds is apt to be nonspecifically adsorbed via ionic bond.

As to the method for labeling DNA, such methods are often used that DNA is labeled from RNA by incorporating a labeled dUTP with a reverse transcription reaction; or that it is labeled from DNA of genome by incorporating a labeled dUTP with a PCR reaction or the like. Although these probes are purified by ethanol precipitation after the reaction, unreacted dye labeled dUTP is often unpurified and left. These unpurified substance often causes nonspecific adsorption.

SUMMARY OF THE INVENTION

An object of the present invention is to solve the aforementioned problems of conventional techniques. That is, the object of the present invention is to provide a method for a DNA micro array which can realize higher detection sensitivity and reproducibility than in conventional techniques, without suffering from effects of nonspecifically adsorbed DNA having a fluorescent dye, unpurified fluorescent dye derivatives or the like.

In order to achieve the above object, the present inventors have studied earnestly, and have found that background of nonspecifically adsorbed fluorescent dye derivatives can be reduced by utilizing a quenching property of the fluorescent dye (when a fluorescent molecule collides with other molecule (quenching agent), excitation energy is scattered and lost to quench fluorescence), thereby completing the invention.

Thus, according to the present invention, there is provided a method for detecting fluorescence by using a solid support to which a probe molecule to be detected is fixed, wherein background is reduced by using a quenching agent.

According to another aspect of the present invention, there is provided a method for blocking a solid support to which a probe molecule to be detected is fixed by using a blocking agent, wherein said blocking agent comprises a quenching agent.

Preferably, the probe molecule to be detected is a nucleotide derivative or its analog, and is more preferably an oligonucleotide, a polynucleotide or a peptide nucleic acid.

Preferably, the solid support is a sheet-like substrate selected from the group consisted of a glass substrate, a resin substrate, a glass or resin substrate which is surface-treated with a silane coupling agent, and a glass or resin substrate having a covering layer on its surface. More preferably, the solid support is a sheet-like substrate selected from the group consisted of a silicate glass substrate, a silicate glass substrate surface-treated with a silane coupling agent, and a silicate glass substrate covered with an organic covering layer.

Preferably, the quenching agent is a fluorescence-quenching compound on fluorescence resonance energy transfer, and is particularly preferably DNP, tetramethyl rhodamine, fluorescein, DABCYL, BODIPYFL, or QSY7dye.

Preferably, the solid support to which the probe molecule to be detected is fixed is manufactured by bringing a reactive solid support provided with a group of reactive linking groups having a reactive group G at or near the end portion of it, which is prepared by reacting a group of charged reactive group X provided on the surface of a solid support with a compound having a reactive group E at or near one end portion of it that can react with said reactive group X to form covalent bond and another reactive group G at or near another end portion of it that is the same as or different from said reactive group E, into contact with a group of probe molecules having a reactive group Q at or near one end portion of it that can react with said reactive group G to form covalent bonding, and binding the probe molecule to the linking group via covalent bonding generated by the reaction between said reactive group Q and said reactive group G.

Preferably, the charged reactive group X is an amino group, a mercapto group or a hydroxyl group.

Preferably, the reactive group E is an ethylenic unsaturated group.

Preferably, the reactive group E is a vinylslulfonyl group represented by the following formula or its derivatives:

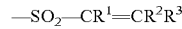

$-SO_2-CR^1=CR^2R^3$ wherein each of $R^1$, $R^2$ and $R^3$ represents independently from each other an atom or a group selected from the group consisted of a hydrogen atom, an alkyl group having 1 to 6 carbon atoms, an aryl group having 6 to 20 carbon atoms, and an aralkyl group having 7 to 26 carbon atoms in total containing an alkyl chain having 1 to 6 carbon atoms.

Preferably, the reactive group G is an ethylenic unsaturated group.

Preferably, the reactive group G is a vinylslulfonyl group represented by the following formula or its derivatives:

wherein each of $R^1$, $R^2$ and $R^3$ represents independently from each other an atom or a group selected from the group consisted of a hydrogen atom, an alkyl group having 1 to 6 carbon atoms, an aryl group having 6 to 20 carbon atoms, and an aralkyl group having 7 to 26 carbon atoms in total containing an alkyl chain having 1 to 6 carbon atoms.

Preferably, the compound having the reactive group E at or near one end portion of it that can react with said reactive group X to form covalent bond and the reactive group G at or near another end portion of it that is the same as or different from the reactive group E is a disulfone compound represented by the following formula:

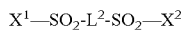

wherein each of $X^1$ and $X^2$ represents independently from each other $-CR^1=CR^2R^3$ or $-CHR^1-CR\,R^3Y$ (reactive precursor group); each of $R^1$, $R^2$ and $R^3$ represents independently from each other an atom or a group selected from the group consisted of a hydrogen atom, an alkyl group having 1 to 6 carbon atoms, an aryl group having 6 to 20 carbon atoms, and an aralkyl group having 7 to 26 carbon atoms in total containing an alkyl chain having 1 to 6 carbon atoms; Y represents an atom or a group selected from the group consisted of a halogen atom, $-OSO_2R^{11}$, $-OCOR^{12}$, $-OSO_3M$, and a quaternary pyridinium group; $R^{11}$ represents a group selected from the group consisted of an alkyl group having 1 to 6 carbon atoms, an aryl group having 6 to 20 carbon atoms, and an aralkyl group having 7 to 26 carbon atoms in total containing an alkyl chain having 1 to 6 carbon atoms; $R^{12}$ represents a group selected from the group consisted of an alkyl group having 1 to 6 carbon atoms and a halogenated alkyl group having 1 to 6 carbon atoms; M represents an atom or a group selected from the group consisted of a hydrogen atom, an alkaline metal atom and an ammonium group; and $L^2$ represents a linking group.

Preferably, 1,2-bis(vinylsulfonylacetamide)ethane is used as the disulfone compound.

Preferably, the reactive group Q is an amino group or a mercapto group.

Preferably, the solid support to which the probe molecule to be detected is fixed is a solid support manufactured by bringing a group of charged groups provided on the surface of a solid support into contact with a group of probe molecules having a charged group at or near one end portion of it that shows, in an aqueous media, a charge which is opposite to the charge shown by said charged groups in the aqueous media, and fixing the probe molecule to the surface of the solid support via electrostatic bond.

Preferably, the charged group that is provided on the surface of the solid support is an amino group, and the charged group in the probe molecule is a phosphate group.

According to further another aspect of the present invention, there is provided a probe molecule-fixed solid support which was subjected to a blocking treatment, which is obtained by the method of the present invention as mentioned above.

According to further another aspect of the present invention, there is provided a method for detecting a sample molecule, comprising the steps of:

bringing a sample containing a sample molecule labeled with a florescent substance into contact with the probe molecule-fixed solid support subjected to a blocking treatment which is obtained by the method of the present invention as mentioned above; and detecting a complex formed between the probe molecule fixed to the solid support and a target substance labeled with the fluorescent substance.

According to further another aspect of the present invention, there is provided a blocking agent for blocking a solid support to which a probe molecule to be detected is fixed, which comprises a quenching agent.

Preferably, the quenching agent is a compound which quenches fluorescence generated from a fluorescent compound by fluorescence resonance energy transfer, and is particularly preferably is DNP, tetramethyl rhodamine, fluorescein, DABCYL, BODIPYFL, or QSY7dye.

DETAILED DESCRIPTION OF THE INVENTION

Hereinafter, the embodiments of the present invention are described in detail.

The present invention relates to a method for detecting fluorescence by using a solid support to which a probe molecule to be detected is fixed, wherein background is reduced by use of a quenching agent.

Further, the present invention relates to a method for blocking a solid support to which a probe to be detected is fixed with a blocking agent, wherein the blocking agent comprises a quenching agent.

In the present invention, the quenching agent contained in a blocking agent may be applied to the solid support, or the quenching agent may be applied to the solid support separately without being contained in the blocking agent. Further, the quenching agent contained in other solution may be applied to the solid support.

Any types of quenching agent may be used in the present invention so long as it can quench fluorescence radiated from a fluorescent compound that is nonspecifically adsorbed to the solid support.

Any compound that can quench an exited singlet state and/or an exited triplet state of a fluorescent compound, can be used as a quenching agent. Examples of the quenching agent include an acceptor molecule (anthraquinone, naphthoquinone, benzoquinone, TCNQ or the like), a nitro compound (trinitrofluorene, dinitroanthracene or the like) and a halogen-containing compound (tribromonaphthalene, triiodonaphthalene or the like) which are described as compounds with a stable exited triplet state in page 6 of Japanese Patent Laid-open Publication No. 2000-94838; aromatic ketones, halogen-containing aromatic compounds and aromatic thioether compuonds which are described in page 9 of Japanese Patent Laid-open Publication No. 2000-502393; and hydrazine compounds described in Japanese Patent Laid-open Publication No. H5-216194.

In the present invention, a fluorescence quenching compound on FRET (Fluorescence Resonance Energy Transfer) (from a fluorescent compound) can be most preferably used since influence of the quenching compound proceeds to a long distance. As for these examples, in addition to quenching agents Dabcyl (in combination with a fluorescent compound Edans), DNP (in combination with fluorescent coumarin, Nma or tryptophan) or the like described in page 18 of Japanese Patent Laid-open Publication No. 2000-503533, a detailed description is made in Handbook of Fluorescent Probes and Research Products 8th Edition (CD-ROM; published by Molecular Probes Co., 2001). For example, the following compounds are listed. In the present invention, the acceptors in the table can be used as a quenching agent.

TABLE 1

| Donor | Acceptor | Ro (Å) |
|---|---|---|
| fluorescein | tetramethyl rhodamine | 55 |
| IAEDANS | fluorescein | 46 |
| EDANS | DABCYL | 33 |
| Fluorescein | fluorescein | 44 |
| BODIPY FL | BODIPY FL | 57 |
| Fluorescein | QSY7 dys | 61 |

Ro: Forster Radius (distance between donor and acceptor when donor activity is 50%)

In the present invention, various dyes based on the principle described in Handbook of Fluorescent Probes and Research Products 8th Edition can be used in addition to above-described examples of an acceptor. Examples of such dyes include, as a typical example, polymethine dyes such as azo dyes and cyanine dyes, and azomethine dyes that are used to form images in a silver halide photographic material.

In a preferable embodiment of the present invention, the solid support and the quenching agent bind each other via covalent bonding. The covalent bond can be formed between a functional group on the solid support and a functional group of the quenching agent. Combinations of the functional group on the solid support and the functional group of the quenching agent are shown below, but are not limited thereto.

TABLE 2

| Reaction Form | Functional group on solid support | Functional group of quenching agent | Reference |
|---|---|---|---|
| amide bond | succinimide | —NH$_2$ | U.S. Pat. No. 5,858,653 |
| amide bond | acid anhydride | —NH$_2$ | JP 8-168399 |
| amide bond | carbodiimido | —NH$_2$ | JP 8-334509 |
| amide bond | triazine | —NH$_2$ | Anal. Chem 53 2090 (1981) |
| amide bond | thioisocyanate | —NH$_2$ | WO 99/64623 |
| 1,4-addition | maleimido | —SH | JP 11-187900 |
| Ring opening | epoxy | —NH$_2$ | P.N.A.S. 82 6379 (1995) |
| C-N bond | aldehyde | —NH$_2$ | |
| C-S bond | iodoacetamide | —SH | WO 98/20020 |
| S-S bond | mercapto | —SH | U.S. Pat. No. 5,837,860 |

Type of a probe molecule used in the present invention is not specifically limited, and any type of substance can be used. Examples thereof include a nucleic acid (DNA or RNA), protein, sugar, their analogs (e.g. peptide nucleic acid) and their complexes (e.g. protein with a sugar chain, or the like). Preferably the probe molecule is nucleic acid, and is most preferably DNA. Hereinafter, the present invention will be described by citing an example where DNA is used as the probe molecule. However, as described above, substances other than DNA can also be used as a probe molecule.

The blocking treatment in the present invention is characterized in that the surface portion of the DNA chip, to which the probe molecule is provided, is treated with a blocking agent containing a quenching agent after manufacture of the DNA chip or before using the DNA chip for an actual detection operation of a sample molecule. The DNA chip to be treated may be of a type in which the probe molecule is fixed to the surface of the chip via covalent bond (hereinafter, referred to as covalent bond type DNA chip), or may be of another type in which the probe molecule is fixed to the surface of the chip via electrostatic bond (hereinafter, referred to as electrostatic bond type DNA chip) or may be of a third type in which the both bonds are formed.

Manufacturing Process of the Covalent Bond Type DNA Chip:

A typical operation of a manufacturing method of the covalent bond type DNA chip includes the following operations: a reactive group such as an amino group that takes a charge in an aqueous solution (positive charge in the case of the amino group) is introduced to the surface of a solid support by treatment with polymer containing the amino group or treatment with silane coupling agent; next a reactive solid support is prepared by bringing the solid support into contact with a bifunctional compound having a group which reacts with the reactive group such as the amino group at one end portion of it and also having a reactive group at another end portion of it; then the reactive solid support is brought into contact with a reactive group of a probe molecule so as to bind and fix the probe molecule to the solid support. Hereinafter, more concrete operations will be described.

First, a group of charged reactive groups X which is provided on surface of a solid support (I), is reacted with a compound (compound that constitute a linking group) which has a reactive group E which is capable of forming covalent bond by reacting with said reactive group X at one end portion of it, and a reactive group G which is the same as or different from the reactive group E at another end portion of it. Thus, a reactive solid support (II), which is provided with a group of reactive linking groups having the reactive group G at or near the end portion of it, is prepared.

Next, the reactive solid support (II) is brought into contact with a group of probe molecules which have a reactive group Q at or near one end portion of them, which is capable of forming covalent bond by reacting with the reactive group G of the reactive solid support (II). Thus, the probe molecules are bound to the linking group via covalent bond formed by the reaction between the reactive group Q and the reactive group G. Thereby, a covalent bond type chip (IIIA) of interest is obtained.

On the covalent bond type DNA chip obtained according to the above-mentioned method, a part of the charged reactive group X (X$^+$) previously introduced to the solid support and a part of the reactive group G of the linking group remain without being reacted. Therefore, in detection operation of a sample molecule, these unreacted groups react with a nucleic acid fragment sample having a reactive group such as an amino group and a portion of a phosphate group and further an anionic fluorescent label, so as to make it be bound and fixed to the surface of the DNA chip without a specific bonding reaction that is the detection reaction. Thus, in detection operation, increase in a background value occurs resulting in deterioration in detection properties such as detection sensitivity. In the present invention, the problem is dissolved by performing the blocking treatment with a quenching agent.

Manufacturing Process of the Electrostatic Bond Type DNA Chip:

A manufacturing process of the electrostatic bond type DNA chip is described bellow.

First, a group of charged group X that is provided on the surface of the solid support (I) is brought into contact with a group of probe molecules having a charged group at or near one end portion of it that shows a charge, in an aqueous media, that is opposite to the charge shown by the charged group X in the aqueous media. Thus, the probe molecules are fixed to the surface of the solid support via electrostatic bond to obtain an electrostatic bond type DNA chip (IIIB).

Blocking Treatment:

Next, blocking treatment of the DNA chips obtained in accordance with the above-described methods is described. The covalent bond type DNA chip (IIIA) or the electrostatic bond type DNA chip (IIIB) is treated with a blocking agent containing a quenching agent so as to make the quenching agent bind to the chip. Then, the thus blocking treated DNA chip (IV) is used for a detection operation of a sample molecule such as a labeled nucleic acid fragment. As described above, by previously binding the quenching agent onto the chip, if the sample molecule nonspecifically binds onto the chip, fluorescence of the sample molecule is quenched by the action of the quenching agent, resulting in reduction of background.

In the chips which are subjected to the blocking treatment according to the present invention, although the types of the solid support are not limited, a substrate having a surface with properties of hydrophobic or low hydrophilic property and smoothness are especially preferable. Further, a substrate that has surface of low smoothness with a convex and a concave can also be used. Examples of the material for the solid support may include ceramics or new ceramics such as glass, cement, or potteries, polymers such as polyethylene terephthalate, cellulose acetate, polycarbonate of bisphenol A, polystyrene, or polymethyl methacrylate, silicon, activated carbon, a variety of porous substances such as porous glass, porous ceramics, porous silicon, porous activated carbon, woven fabric, knitted fabric, non-woven fabric, filter paper, short fiber, or membrane filter. It is preferable that the size of a fine hole of the porous substance is in the range of 2 to 1000 nm, and particularly preferable in the range of 2 to 500 nm. It is particularly preferable that material of the solid support is glass or silicon. This is because of the easiness of surface treatment and the easiness of analysis by an electrochemical method. It is preferable that the thickness of the solid support is in the range of 100 to 2000 μm.

As the above-described solid support, a variety of solid supports, which have been conventionally used in manufacture of DNA chips or proposed for manufacture of DNA chips, can be preferably used. Examples of such solid supports include a glass substrate, a resin substrate, a glass substrate or a resin substrate which is surface-treated with a silane coupling agent, a glass substrate or a resin substrate having a covering layer on its surface, or the like. It is particularly preferable that the solid support is made of a silicate glass substrate, a silicate glass substrate which is surface-treated with a silane coupling agent, a silicate glass substrate covered with an organic covering layer. Also, an electrode substrate used as a substrate of a DNA chip used for an electrochemical analyzing method may also be utilized. Further, a variety of functional substrates such as a substrate used for a surface plasmon resonance (SPR) biosensor, a charge coupled device (CCD) or the like may also be utilized. Furthermore, a particle-like solid support may also be used other than those substrates.

For the purpose of fixing a bifunctional reactive compound such as a divinylsulfone compound by covalent bond, or of electrostatically fixing a sample molecule having a charged group (e.g. DNA fragment), the surface of the solid support is preferably subjected to a covering treatment with polymer having, on its side chain, an amino group (in this case, the amino group is the reactive group that is introduced to the surface of the solid support) such as a polycationic compound (for example, poly-L-lysine, polyethyleneimine, polyalkylamine or the like is preferable, and poly-L-lysine is more preferable). Alternatively, the surface of the solid support may be surface-treated with a surface treatment agent such as a silane coupling agent which has a reactive group that can react with the surface of the solid support and another reactive group such as the amino group.

In the case where the covering treatment is performed with a polycationic compound, an amino group is introduced to the surface of the solid support by electrostatically binding between the polymer compound and the surface of the solid support. On the other hand, in the case where the surface treatment is performed by a silane coupling agent, the amino group and the like stably exists on the surface of the solid support since it is bound and fixed to the surface of the solid support by covalent bond. In addition to an amino group or a mercapto group, an aldehyde group, a carboxyl group or a hydroxyl group may be also preferably introduced.

As a silane coupling agent having an amino group, it is usual to use γ-aminopropyltriethoxy silane, N-β(aminoethyl)-γ-aminopropyltrimethoxy silane, or N-β(aminoethyl)-γ-aminopropylmethyldimethoxy silane.

The treatment with a silane coupling agent may be performed in combination with the treatment using a polycationic compound. Using this method, an electrostatical interaction between a hydrophobic- or a low hydrophilic-solid support and DNA fragments can be promoted. A layer consisted of a hydrophilic polymer having a charge or the like or a layer consisted of a crosslinking agent may be further provided on the surface of the solid support treated by a polycationic compound. As a result of providing such a layer, the height of the convex and concave portions of the solid support treated by the polycationic compound can be reduced. Depending on the types of the solid supports, it is possible that a hydrophilic polymer is contained in the support.

On the surface of usually utilized solid supports for a DNA chip, large number of regions previously fractioned or supposed are set and provided. In each region, a reactive group which takes a charge in an aqueous media such as an amino group or a nonreactive group is previously introduced. To the surface of each region of the solid support used, a charged reactive group such as an amino group or a hydroxyl as described above is provided. However, to a solid support not having such a reactive group, introduction of a reactive group is performed as described above, by surface treatment using a silane coupling agent, or by utilizing a method of coating and covering polymer having a reactive group such as an amino group on side chain on the surface of the solid support.

Examples of commercially available solid supports that are previously subjected to one of the above-described surface treatments include PLL (Sigma Co.: poly-L-lysine coating) CMT-GAPS (Corning Co.: aminosilane coating), MAS (Matsunami Glass Co., LTD: aminosilane coating), Silanate (Gryner Co.: polysilane coating), Silanate (Telechem: polysilane coating), DNA-Ready Type 1 or 2 Slide (Clonetech Co.: aminosilane coating), Silirate (Gryner Co.:silane aldehyde coating) 3D-Link (Thermotechs Co.: activated carbonic acid treatment) and the like.

A typical covalent bond type chip that is the subject of the blocking treatment according to the present invention may be manufactured by using a reactive solid support provided with a linking group having a vinylsulfonyl group at or near the end portion of it, which is prepared by bringing a solid support provided with a charged reactive group into contact with a bifunctional compound such as a divinylsulfone compound.

The above-mentioned reactive solid support may be manufactured by preparing a solid support previously provided with a reactive group on its surface, then bringing the solid support into contact with a compound having a reactive group at or near its end portion that can react with the reactive group provided on the surface of the solid support to form covalent bond and a vinylsulfonyl group or its reactive precursor group at or near another end portion of it.

That is, by bringing the solid support provided with a reactive group into contact with a bifunctional reactive compound such as a divinylsulfone compound, the reactive group and the bifunctional reactive compound react each other to form covalent bond; a portion of the reactive group on the solid support is elongated; a reactive chain having a vinylsulfonyl group or its reactive precursor group at or near its end portion is formed; thus the reactive solid support is obtained.

In the reactive solid support, a linker composed of a vinylsulfonyl group or its reactive precursor group and a linking group introduced to the surface of the solid support is desirably a linker represented by the following formula (1):

$$-L-SO_2-X \qquad (1)$$

In the above-described formula (1), X represents $-CR^1=CR^2R^3$ or $-CHR_1-CR^2R^3Y$ (reactive precursor group). Each of $R^1$, $R^2$ and $R^3$ represents independently from each other a hydrogen atom, an alkyl group having 1 to 6 carbon atoms, an aryl group having 6 to 20 carbon atoms, or an aralkyl group having 7 to 26 carbon atoms in total containing an alkyl chain having 1 to 6 carbon atoms. Examples of an alkyl group having 1 to 6 carbon atoms include a methyl group, an ethyl group, an n-propyl group, an n-butyl group, and an n-hexyl group. A methyl group is particularly preferable. Aryl groups include a phenyl group and a naphthyl group. It is preferable that each of $R^1$, $R^2$ and $R^3$ represents a hydrogen atom, respectively.

Y represents a group which is substituted by a nucleophilic reagent such as $-OH$, $-OR^0$, $-SH$, $NH_3$, $NH_2R^0$ (wherein $R^0$ represents a group such as alkyl group except for hydrogen atom), or a group which is eliminated as "HY" by base. Examples thereof include a halogen atom, $-OSO_2R^{11}$, $-OCOR^{12}$, $-OSO_3M$, or a quaternary pyridinium group ($R^{11}$ represents an alkyl group having 1 to 6 carbon atoms, an aryl group having 6 to 20 carbon atoms, or an aralkyl group having 7 to 26 carbon atoms in total containing an alkyl chain having 1 to 6 carbon atoms; $R^{12}$ represents an alkyl group having 1 to 6 carbon atoms or halogenated alkyl group having 1 to 6 carbon atoms; M represents a hydrogen atom, an alkaline metal atom, or an ammonium group).

L represents a bivalent or more than bivalent linking group for linking the solid support or a linking group binding to the solid support with the above-described $-SO_2-X$ group. However, L may be a single bond. Examples of the bivalent linking groups include an alkylene group having 1 to 6 carbon atoms, an aliphatic cyclic group having 3 to 16 carbon atoms, an arylene group having 6 to 20 carbon atoms, a heterocyclic group having 2 to 20 carbon atoms containing 1 to 3 hetero atoms selected from the group consisted of N, S and P, a group containing one group or the combination of a plurality of groups selected from the group consisted of $-O-$, $-S-$, $-SO-$, $-SO_2-$, $-SO_3-$, $-NR^{11}-$, $-CO-$ and their combinations. $R^{11}$ is preferably a hydrogen atom, an alkyl group having 1 to 15 carbon atoms, an aryl group having 6 to 20 carbon atoms, or an aralkyl group having 7 to 21 carbon atoms containing an alkyl group having 1 to 6 carbon atoms, and more preferably a hydrogen atom or an alkyl group having 1 to 6 carbon atoms, and particularly preferably a hydrogen atom, a methyl group or an ethyl group. In the case where L represents a group containing the combination of two or more of the groups selected from the group consisted of $-NR^{11}-$, $-SONR^{11}-$, $-CONR^{11}-$, $-NR^{11}COO-$, and $-NR^{11}CONR^{11}-$, these $R^{11}$ may bind each other to form a ring.

An alkyl group of $R^{11}$, an aryl group of $R^{11}$ and an aralkyl group of $R^{11}$ may have a substituent. Such substituents include an atom or a group selected from the group consisted of a hydroxyl group, an alkoxy group having 1 to 6 carbon atoms, an alkenyl group having 1 to 6 carbon atoms, a carbomoyl group having 2 to 7 carbon atoms, an alkyl group having 1 to 6 carbon atoms, an aralkyl group having 7 to 16 carbon atoms, an aryl group having 6 to 20 carbon atoms, an sulfamoyl group (or its Na salt, K salt or the like) a sulfo group (or its Na salt, K salt or the like), a carboxylic acid group (or its Na salt, K salt or the like), a halogen atom, an alkenylene group having 1 to 6 carbon atoms, an arylene group having 6 to 20 carbon atoms, sulfonyl group and their combinations.

As for L, a group obtained by substituting a hydrogen atom of the alkylene group of the above formula with a $-SO_2CH=CH_2$ group is also preferable.

As for a bifunctional reactive compound utilized for obtaining a solid support to which a vinyl sulfonyl group represented by the foregoing formula (1) or its reactive precursor group is fixed by covalent bond, a disulfone compound represented by the following formula (2) can be advantageously utilized.

$$X^1-SO_2-L^2-SO_2-X^2 \qquad (2)$$

[In the above-described formula, each of $X^1$ and $X^2$ represents independently from each other $-CR^1=CR^2R^3$ or $-CHR^2-CR^2R^3Y$ (reactive precursor group); each of $R^1$, $R^2$ and $R^3$ represents independently from each other an atom or a group selected from the group consisted of a hydrogen atom, an alkyl group having 1 to 6 carbon atoms, an aryl group having 6 to 20 carbon atoms, and an aralkyl group having 7 to 26 carbon atoms in total containing an alkyl chain having 1 to 6 carbon atoms; Y represents an atom or a group selected from the group consisted of a halogen atom, $-OSO_2R^{11}$, $-OCOR^{12}$, $-OSO_3M$ and quaternary pyridinium group; $R^{11}$ represents a group selected from the group consisted of an alkyl group having 1 to 6 carbon atoms, an aryl group having 6 to 20 carbon atoms and an aralkyl group having 7 to 26 carbon atoms in total containing an alkyl chain having 1 to 6 carbon atoms; $R^{12}$ represents a group selected from the group consisted of an alkyl group having 1 to 6 carbon atoms and a halogenated alkyl group having 1 to 6 carbon atoms; M represents an atom or a group selected from the group consisted of a hydrogen atom, an alkali metallic atom and an ammonium group; and $L^2$ represents a linking group].

Specifically, the aforementioned reactive solid support can be easily manufactured by bringing a disulfone compound represented by the above-described formula (2) into contact with the above mentioned solid support, for example in the aqueous atmosphere.

Representative examples of disulfone compound represented by the above-described formula (2) include 1,2-bis(vinylsulfonylacetamide)ethane.

As for a method for synthesizing a disulfone compound used for the production of a reactive solid support, the details have been described in a variety of gazettes, for example, such as Japanese Patent Publication No.S47-2429, Japanese Patent Publication No.S50-35807, Japanese Unexamined Patent Publication No.S49-24435, Japanese Unexamined Patent Publication No.S53-41551, Japanese Unexamined Patent Publication No.S59-18944 or the like.

In order to prepare a detection tool (which is referred to as a DNA chip in general) for detecting by fixing a polynucleotide or an oligonucleotide originated in the nature such as DNA, RNA, a DNA fragment, an RNA fragment or the like by utilizing the reactive solid support (II), such a method can be utilized, as described above, that the reactive solid support (II) is brought into contact with a nucleotide derivative or its analog provided with a reactive group such as an amino group (amino group is positively charged in an aqueous medium) or the like which reacts with a vinylsulfonyl group or its reactive precursor group on the surface of the support to form covalent bond. That is to say, a detection tool equipped with a probe molecule composed of the desired nucleotide derivative or its analog (so called DNA chip) can be prepared in this way.

A vinyl sulfonyl group or its reactive precursor group bound via covalent bond to the surface of a solid support can be readily preserved in a stable state since it has a high resistance to the hydrolysis, and can form a stable covalent bond by rapidly reacting with a nucleotide derivative or a reactive group of its analog in which amino group has been previously provided or a reactive group such as amino group has been introduced.

As described above, types of probe molecules used in the present invention is not particularly limited, and any material can be utilized. Among them, nucleotide derivatives or their analogs are preferable. Representative examples of a nucleotide derivative and its analog used as a probe molecule include an oligonucleotide, a polynucleotide, and a peptide nucleic acid. These nucleotide derivatives or their analogs may be originally from the nature (DNA, DNA fragment, RNA or RNA fragment), or may be a synthetic compound. Moreover, nucleotide derivatives or its analog include a variety of analogous compounds such as what is called a LNA having a crosslinking group at its sugar unit portion (J. Am. Chem. Soc. 1998, 120:13252–13253).

In the case where DNA fragments are used as a probe molecule, these are divided into two types depending on purposes. In order to examine the expression of a gene, it is preferable to use a polynucleotide such as cDNA, one portion of cDNA, or EST. Functions of these polynucleotides may be unknown, but in general, these are prepared by amplifying cDNA library, genomic library, or the total genome as a template on the basis of the sequences registered on a data base by a PCR method (hereinafter, referred to as "PCR product"). Ones not amplified by a PCR method can also be preferably used. In order to examine the mutation and polymorphism of a gene, it is preferable to synthesize a variety of oligonucleotides corresponding to mutation and polymorphism based on the known sequence which is to be the standard, and use them. Furthermore, in the case where the purpose is to analyze the base sequence, it is preferable to synthesize $4^n$ (n represents the length of the base) species of oligonucleotides and use them. As for the base sequence of a DNA fragment, it is preferable that its sequence has been previously determined by a general base sequence determination method. The size of the DNA fragment is preferably from dimmer to 50-mer, and particularly preferably from 10- to 25-mer.

On one end of a nucleotide derivative such as an oligonucleotide and a DNA fragment, or its analog, a reactive group which forms a covalent bond by reacting with the foregoing vinyl sulfonyl group or its reactive precursor group is introduced. Such reactive groups are preferably an amino group, an imino group, hydrazino group, carbomoyl group, hydrazinocarbonyl group or carboxyimido group, and the amino group is particularly preferable. The reactive group is usually bound to an oligonucleotide or a DNA fragment via a crosslinker. As the crosslinker, for example, an alkylene group or a N-alkylamino-alkylene group is utilized, and a hexylene group or a N-methylamino-hexylene group is preferable, and a hexylene group is particularly preferable. It should be noted that since a peptide nucleic acid (PNA) has an amino group, usually it is not necessary to introduce another reactive group.

A bifunctional compound (or it may be trifunctional or more) used for manufacture of the covalent bond type DNA chip is, needless to say, not to be limited to the above-mentioned divinylsulfonyl compound.

As mentioned above, the blocking treatment according to the present invention may also be used for the electrostatic bond type DNA chip in which a probe molecule is bound via electrostatic bond. As a typical example of the DNA chip in which the probe molecule is bound via electrostatic bond, a DNA chip can be listed that is prepared by bringing a DNA fragment probe having a phosphate group into contact, in the presence of an aqueous medium, with a solid support to the surface of which an amino group is introduced so as to form electrostatic bond by utilizing a positive charge of an amino group and a negative charge of a phosphate group.

A blocking agent used for the blocking treatment in the present invention contains a quenching agent, and is usually an aqueous solution.

In addition to the quenching agent, the blocking agent used in the present invention may further contain a charged compound that is used as a blocking agent or a surfactant such as an anionic surfactant.

Specifically, in the case where an amino group is introduced as a charged reactive group to the surface of the solid support and a vinylsulfonyl group is a reactive group provided near the end portion of a linking group, it is preferred to use compounds of high molecular weight having an acidic group, such as dextran sulfate, mucopolysaccharides having a sulfonyl group, taurine having a sulfonyl group, polypeptide having a carboxyl group, polysaccharide having a carboxyl group, as a charged compound for the blocking treatment. It is preferred to use compounds having an active hydrogen such as an amino group, a mercapto group, or a hydroxyl group (e.g. glycine) as a compound that can inactivate the reactive group. Glycine is preferable since it can also function as a buffer in the above-described blocking treatment. Further, taking account of an ionic atmosphere of the utilized blocking treatment, any surfactant can be selected from anionic surfactants (for example, alkylbenzene sulfonate, lauryl sulfate ester, sulfosuccinate octyl ester, stearate soap or the like), nonionic surfactants (for example, nonyl phenol, lauryl alcohol, polyethylene glycol or the like) and cationic surfactants (for example, cetyl pyridinium chloride, lauryl dimethyl benzyl ammonium chloride, stearyl trimethyl ammonium chloride or the like).

Also, in addition to the quenching agent, the blocking agent used for treatment of the electrostatic bond type DNA chip may further contain a charged compound which shows a charge in an aqueous medium, which is opposite to the charge shown by the charged group introduced to the surface of the solid support of the chip in the aqueous medium. An surfactant as mentioned above may preferably be added to an aqueous solution containing a blocking agent.

Specifically, in the case where an amino group which is positively charged in an aqueous medium is introduced to the surface of the solid support, it is preferred to use a compound of high molecular weight having an acidic group such as dextran sulfate, mucopolysaccharides having a sulfonyl group, taurine having a sulfonyl group, polypeptide having a carboxyl group, or polysaccharide having a carboxyl group, as a charged compound for the blocking treatment. It is also preferred to add a buffer compound such as glycine that has buffering function in the blocking treatment. Therefore, the above-described blocking agent which is used for the blocking treatment of the covalent bond type DNA chip, can be also used for the blocking treatment of the electrostatic bond type DNA chip.

Detection of a sample molecule with the chip that is subjected to the blocking treatment according to the method of the present invention can be performed by performing procedures in the same way as in the detection procedures of a complementary nucleic acid fragment sample using known DNA chips.

As a nucleic acid fragment sample, usually, a nucleic acid fragment sample such as a DNA fragment sample or a RNA fragment sample whose sequence and function is not known is used.

It is preferable that a nucleic acid fragment sample is isolated from the cell or tissue sample of eucaryote for the purpose of examining the gene expression. In the case where the sample is a genome, it is preferably isolated from any given tissue sample except for red blood cell. It is preferable that any given tissue except for red blood cell is peripheral blood lymphocyte, skin, hair, sperm or the like. In the case where the sample is an mRNA, it is preferable that it is extracted from the tissue sample in which the mRNA is expressed. It is preferable that a labeled cDNA is prepared from mRNA by incorporating a labeled dNTP ("dNTP" means a deoxyribonucleotide in which the base is adenine (A), cytosine (C), guanine (G) or thymine (T)) using reverse transcription reaction. As a dNTP, use of dCTP is preferable because of chemical stability. Although the amount of the mRNA required for one hybridization is different depending on the amount of liquid to be spotted, and the type of labeling material, it is several μg or less. It is desired that the nucleic acid fragment sample has been previously depolymerized in the case where a DNA fragment on the nucleotide derivative or its analog fixed solid support is an oligoDNA. In the case of a prokaryotic cell, since the selective extraction of an mRNA is difficult, it is preferable that the total RNA is labeled.

For the purpose of detecting mutation or polymorphism of a gene, the nucleic acid fragment sample is preferably obtained by performing PCR of a target region in a reaction system containing a labeled primer or a labeled dNTP.

In general, a nucleic acid fragment sample is labeled in various ways to permit detection of the sample bound and fixed by hybridization. As labeling methods, although a RI method and a non-RI method (fluorescence method, biotin method, chemiluminescence method or the like) are known, it is preferred in the present invention to use fluorescence method. As a fluorescent substance utilized for a fluorescence labeling, any can be used if it can bind to the basic portion of nucleic acid. For example, cyanine dye (e.g., Cy3, Cy5 or the like of Cy Dye™ series, which is commercially available), rhodamine 6G reagent, N-acetoxy-N2-acetylaminofluorene (AAF) or AAIF (iodine derivative of AAF) can be used.

In general, hybridization is performed by dotting an aqueous liquid in which labeled nucleic acid fragment samples are dissolved or dispersed, which have been previously pipetted into a 96 wells or a 384 wells plastic plate, to the surface of the solid support (chip) to which the probe molecule is fixed. Usually the amount of the aqueous liquid to be dotted is in a range of 1 to 100 nL. The hybridization is generally carried out in the temperature range of room temperature to 70° C., and in the period of 6 to 20 hours. After the termination of the hybridization, washing is performed using a mixture solution of a surfactant and a buffer to remove unreacted nucleic acid fragment samples. As the surfactant, sodium dodecyl sulfate (SDS) is usually used. As the buffer solution, a citrate buffer, a phosphate buffer, a borate buffer, TRIS buffer, Good' buffer solution or the like is usually used.

The present invention will be more concretely described with the following examples, but the present invention is not limited by these examples.

EXAMPLES

Example 1

Study of Blocking Effect with Fluorescence Quenching Agent (1) Preparation of DNA Fragment A DNA fragment (454 bp) was prepared by performing PCR using the following DNAs having a specific sequence derived from human liver.

primer (U): ACCCCCGGAAAACACGCACAGT (SEQ ID NO.1)

primer (L): TCAGGCACTTTCATTAACAGGCACA (SEQ ID NO.2)

PCR was performed for fixation using one of the above-mentioned primer of which 5' end was modified with an amino group; while PCR was performed for detection using another primer of which 5' end was fluorescently labeled with FlouroLink Cy5 (manufactured by Amersham Pharmacia Biotech Co.).

(2) Preparation of Solid Support to which Vinylsulfonyl Group is Introduced

After immersing a slide glass (25 mm×75 mm) in an ethanol solution of aminopropylethoxy silane (2% by weight) (Shin-Etsu Chemical) for 10 minutes, the slide glass was taken out of the solution. Then, it was washed with ethanol, dried at 110° C. for 10 minutes to prepare a silane compound-coated slide glass (A). Then, the silane compound-coated slide glass (A) was immersed in a phosphate buffer solution (pH=8.5) of 1,2-bis (vinylsulfonylacetamide) ethane (5% by weight) for 1 hour. Then, the slide glass was taken out of the solution, washed with acetonitrile, dried for 1 hour under a reduced pressure. Thus, a solid support (B) to the surface of which the vinylsulfonyl group was introduced was obtained.

(3) Fixation of DNA

An aqueous liquid ($1 \times 10^{-6}$ M) prepared by dispersing the DNA fragment for fixation prepared in the above (1) in sterilized water was dotted to the solid supports (B) obtained in the above (2) (slide glass to the surface of which vinylsulfonyl group is introduced) with a spotting device.

The solid supports after the dotting were left all night in a chamber conditioned with the saturated saline solution in order to sufficiently progress the bonding reaction between the solid support and the DNA.

(4) Blocking

Next, blocking treatment was performed according to the following blocking conditions:

blocking agent (1): 0.1M of Gly, 0.1M of NaCl (pH=8.5) and 0.2% of SDS;

blocking agent (2): 50 mM of boric acid, 50 mM of KCl (pH=8.5), 0.2% of SDS and 10 mM of DABSYL-amine.

Respective slide glasses to which DNA fragments were dotted were placed in slide glass racks, and were shaken up and down in dying trays containing the above-described blocking agent respectively, for 30 minutes to perform blocking.

After the respective blocking treatments, the slide glasses were immersed in boiled water of 95° C. for 3 minutes, and then immersed in chilled ethanol for 3 minutes, then dried at room temperature.

(5) Hybridization

An aqueous liquid, which was prepared by dispersing the above-described DNA for detection in a hybridization solution (5× SSC solution and 0.5 wt % of SDS; 50 µL) to be the concentration of $1 \times 10^{-6}$ M, was dotted to the above-described respective solid support. After protecting the surface of the solid supports with a cover glass for microscopy, the solid supports were incubated in a moisture-conditioned chamber at 60° C. for 20 hours. Then, the solid supports were sequentially washed with a mixed solution of 0.1 wt % SDS and 2×SSC at room temperature, with a mixed solution of 0.1 wt % SDS and 0.2×SSC at 37° C. and with an aqueous solution of 0.2×SSC at room temperature. Next, the solid supports were centrifuged at 600 rpm for 20 seconds and dried at room temperature.

Background (fluorescence intensity) of the respective slide glasses were compared each other. The result is shown in Table 3 bellow.

TABLE 3

| Type of Blocking Agent | Value of Background |
| --- | --- |
| blocking agent (1) | 12000 |
| blocking agent (2) | 2500 |

From the result shown in Table 3, it is understood that background is certainly reduced by use of the quenching agent.

Effect of the Invention

The present invention can provide a novel method for reducing background in fluorescence detection. By using the present invention, detection sensitivity of a DNA chip can be increased and stable data can be obtained.

What is claimed is:

1. A method for reducing background in fluorescence detection, which comprises:

treating a solid support, to which a probe molecule to be detected is fixed, with a quenching agent so as to bind the quenching agent to the solid support; and bringing a sample containing a sample molecule labeled with a fluorescent substance into contact with the probe molecule-fixed solid support;

wherein background fluorescence caused by non-specific binding of the sample molecule is quenched by the action of the quenching agent, and wherein the solid support to which the probe molecule to be detected is fixed is manufactured by:

reacting a group of a charged reactive group X provided on the surface of a solid support with a compound having (a) a reactive group E at or near one end portion that can react with said reactive group X to form covalent bonding and (b) a reactive group G at or near another end portion that is the same as or different from said reactive group E, wherein said reaction between reactive groups E and X form a reactive solid support;

bringing said reactive solid support that is provided with a group of reactive linking groups into contact with a group of probe molecules having a reactive group Q at or near one end wherein said reactive group Q reacts with said reactive group G to form covalent bonding; and binding the probe molecule to the linking group via covalent bonding generated by the reaction between said reactive group Q and said reactive group G.

2. The method according to claim 1, wherein the probe molecule to be detected is a nucleotide derivative or its analog.

3. The method according to any of claim 1, wherein the probe molecule to be detected is an oligonucleotide, a polynucleotide or a peptide nucleic acid.

4. The method according to claim 1, wherein the solid support is a sheet-like substrate selected from the group consisted of a glass substrate, a resin substrate, a glass or resin substrate which is surface-treated with a silane coupling agent, and a glass or resin substrate having a covering layer on its surface.

5. The method according to claim 1, wherein the solid support is a sheet-like substrate selected from the group consisted of a silicate glass substrate, a silicate glass substrate surface-treated with a silane coupling agent, and a silicate glass substrate covered with an organic covering layer.

6. The method according to claim 1, wherein the quenching agent is DNP, tetramethyl rhodamine, fluorescein, DABCYL, BODIPYFL, or QSY7dye.

7. The method according to claim 1, wherein the charged reactive group X is an amino group, a mercapto group or a hydroxyl group.

8. The method according to claim 1, wherein the reactive group E is an ethylenic unsaturated group.

9. The method according to claim 1, wherein the reactive group E is a vinyislulfonyl group represented by the following formula or its derivatives:

$$-SO_2-CR^1=CR^2R^3$$

wherein each of $R^1$, $R^2$ and $R^3$ represents independently from each other an atom or a group selected from the group consisted of a hydrogen atom, an alkyl group having 1 to 6 carbon atoms, an aryl group having 6 to 20 carbon atoms, and an aralkyl group having 7 to 26 carbon atoms in total containing an alkyl chain having 1 to 6 carbon atoms.

10. The method according to claim 1, wherein the reactive group G is an ethylenic unsaturated group.

11. The method according to claim 1, wherein the reactive group G is a vinyislulfonyl group represented by the following formula or its derivatives:

$$-SO_2-CR^1=CR^2R^3$$

wherein each of $R^1$, $R^2$ and $R^3$ represents independently from each other an atom or a group selected from the group consisted of a hydrogen atom, an alkyl group having 1 to 6 carbon atoms, an aryl group having 6 to 20 carbon atoms, and an aralkyl group having 7 to 26 carbon atoms in total containing an alkyl chain having 1 to 6 carbon atoms.

12. The method according to claim 1, wherein the compound having the reactive group E at or near one end portion of it that can react with said reactive group X to form covalent bond and the reactive group G at or near another end portion of it that is the same as or different from the reactive group B is a disulfone compound represented by the following formula:

$$X^1-SO_2-L^2-SO_2-X^2$$

wherein each of $X^1$ and $X^2$ represents independently from each other $-CR^1=CR^2R^3$ or $-CHR^1-CR^2R^3Y$ (reactive precursor group); each of $R^1$, $R^2$ and $R^3$ represents independently from each other an atom or a group selected from the group consisted of a hydrogen atom, an alkyl group having 1 to 6 carbon atoms, an aryl group having 6 to 20 carbon atoms, and an aralkyl group having 7 to 26 carbon atoms in total containing an alkyl chain having 1 to 6 carbon atoms; Y represents an atom or a group selected from the group consisted of a halogen atom, $-OSO_2R^{11}$, $-OCOR^2$, $-OSO_3M$, and a quaternary pyridinium group; $R^{11}$ represents a group selected from the group consisted of an alkyl group having 1 to 6 carbon atoms, an aryl group having 6 to 20 carbon atoms, and an aralkyl group having 7 to 26 carbon atoms in total containing an alkyl chain having 1 to 6 carbon atoms; $R^{12}$ represents a group selected from the group consisted of an alkyl group having 1 to 6 carbon atoms and a halogenated alkyl group having 1 to 6 carbon atoms; M represents an atom or a group selected from the group consisted of a hydrogen atom, an alkaline metal atom and an ammonium group; and $L^2$ represents a linking group.

13. The method according to claim 12, wherein 1,2-bis(vinylsulfonylacetamide)ethane is used as the disulfone compound.

14. The method according to claim 1, wherein the reactive group Q is an amino group or a mercapto group.

15. The method according to claim 1, wherein the solid support to which the probe molecule to be detected is fixed is a solid support manufactured by bringing a group of charged groups provided on the surface of a solid support into contact with a group of probe molecules having a charged group at or near one end portion of it that shows, in an aqueous media, a charge which is opposite to the charge shown by said charged groups in the aqueous media, and fixing the probe molecule to the surface of the solid support via electrostatic bond.

16. The method according to claim 15, wherein the charged group that is provided on the surface of the solid support is an amino group, and the charged group in the probe molecule is a phosphate group.

* * * * *